United States Patent [19]

Bertolini et al.

[11] Patent Number: 5,221,770
[45] Date of Patent: Jun. 22, 1993

[54] PROCESS FOR THE PREPARATION OF 2-AMINO-5,6-DIMETHOXY-TETRALIN

[75] Inventors: Giorgio Bertolini, Sesto San Giovanni; Cesare Casagrande, Arese; Francesco Santangelo, Milan, all of Italy

[73] Assignee: Zambon Group S.p.A., Venice, Italy

[21] Appl. No.: 950,484

[22] Filed: Sep. 25, 1992

[30] Foreign Application Priority Data

Sep. 26, 1991 [IT] Italy ................. MI 91 A 002560

[51] Int. Cl.⁵ .................................. C07C 211/38
[52] U.S. Cl. ........................... 564/428; 564/396; 564/414
[58] Field of Search ............. 564/396, 428, 446, 462, 564/214, 414; 562/459, 442

[56] References Cited

U.S. PATENT DOCUMENTS

| | | | |
|---|---|---|---|
| 4,163,063 | 7/1979 | Cannon et al. | 424/330 |
| 4,410,519 | 10/1983 | Seiler et al. | 424/226 |
| 4,876,284 | 10/1989 | Arvidsson et al. | 514/657 |
| 4,975,461 | 12/1990 | Misra | 514/510 |

OTHER PUBLICATIONS

McDermed et al. "Synthesis and Pharmacology of Some 2-aminotetralins." *J. Med. Chem.* 18(4): 362–67 Apr. 1975.
Mitsuhashi et al. CA77: 126288h (1972).
Varie *Tetrahedon Letters* 31(52):7583–86 (1990).

*Primary Examiner*—Allen J. Robinson
*Assistant Examiner*—Brian M. Burn
*Attorney, Agent, or Firm*—Oblon, Spivak, McClelland, Maier & Neustadt

[57] ABSTRACT

A process is disclosed for the preparation of 2-amino-5,6-dimethoxy-tetralin, which is a useful intermediate for the preparation of pharmacologically active chemical compounds.

4 Claims, No Drawings

PROCESS FOR THE PREPARATION OF 2-AMINO-5,6-DIMETHOXY-TETRALIN

DESCRIPTION

The present invention relates to a process for the preparation of 2-amino-tetralin and, more particularly, a process for the preparation of 2-amino-5,6-dimethoxy-tetralin.

2-amino-5,6-dimethoxy-tetralin, or rather 2-amino-5,6-dimethoxy-1,2,3,4-tetrahydronaphthalene, is a chemical compound known as a dopamine analogue and has been widely described in the literature, above all as a useful intermediate for the preparation of several pharmacologically active chemical compounds.

Examples of such compounds are: 2-amino-5,6-dihydroxy-1,2,3,4-tetra-hydronaphthalene (generally referred to as 5,6-ADTN) with dopaminergic activity and 5,6-dimethoxy-tetralin with emetic activity as described by Sprenger et al. in J. Med. Chem., 12, 487–490, (1969), 1,2,3,4-tetrahydronaphthalins with bronchodilating activity as described in the French patent No. 2528422 (Chiesi Farmaceutici S.p.A.), and chemical compounds with dopaminergic activity and alpha$_1$-antagonists as described in EP-A-0 321 968 (SIMES, Società Italiana Medicinali e Sintetici S.p.A.).

Several synthesis of 2-amino-5,6-dimethoxy-tetralin have been described in the literature.

For example: a synthesis which requires the preparation of 5,6-dimethoxy-1-tetralone, its transformation to the corresponding oxime tosylate, rearrangement to 2-amino-5,6-dimethoxy-1-tetralone and finally reduction of the ketonic group (as described in the aforementioned work of Sprenger et al.), and some syntheses which require the preparation of 5,6-dimethoxy-2-tetralone and its transformation to the corresponding amino derivative by reductive amination with sodium cyanoborohydride and ammonium acetate [Cannon et al., J. Med. Chem., 20, 1111–1116, (1977) and Horn et al. J. Med. Chem., 21, 825–828, (1978)].

However, to our knowledge, none of the syntheses described in the literature has an industrial application.

In fact, in certain cases, these syntheses require the use of reactants which cannot be used industrially or involve reactions which are long and troublesome.

Moreover, the known syntheses for the preparation of 2-amino-5,6-dimethoxy-tetralin have a very low overall yield.

We have found a process suitable for industrial use for the preparation of 2-amino-5,6-dimethoxy-tetralin and this is an object of the present invention.

The process of this invention is illustrated by the following scheme, which is then explained and described in detail.

Scheme 1

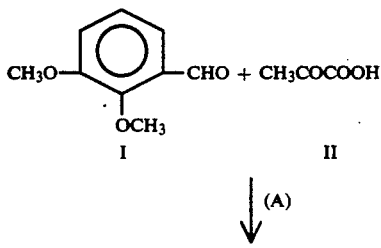

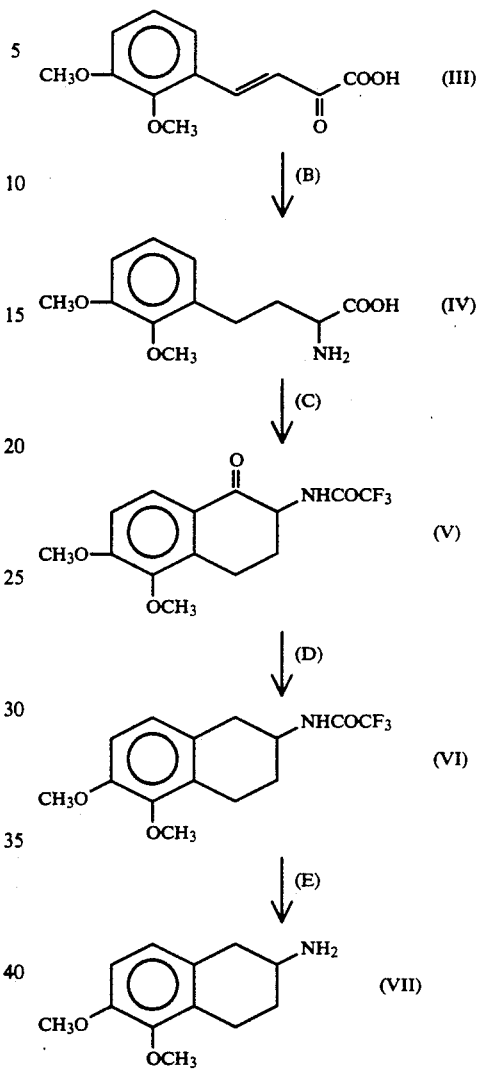

where the asterisk indicates an asymmetric carbon atom.

The steps indicated above are as follows:

A) condensation reaction of 2,3-dimethoxy-benzaldehyde (I) with pyruvic acid (II), in the presence of a base, to form 4-(2,3-dimethoxyphenyl)-2-oxo-3-butenoic acid (III);

B) transformation of the ketonic group of compound (III) to an amino group and reduction of the double bond to obtain 2-amino-4-(2,3-dimethoxyphenyl)-butanoic acid (IV);

C) cyclization, with trifluoroacetic acid and trifluoroacetic anhydride, of compound (IV) with concomitant protection of the amino group to form in a single step 5,6-dimethoxy-2-trifluoroacetylamino-1-tetralone (V);

D) reduction of the ketonic group of compound (V) to yield 5,6-dimethoxy-2-trifluoroacetylamino-tetralin (VI); and E) deprotection of the amino group of compound (VI) to obtain 2-amino-5,6-dimethoxy-tetralin (VII).

Compound (VII) thus obtained can be demethylated using conventional procedures to obtain 5,6-ADTN or derivatized at the nitrogen atom to obtain, for example, compounds with pharmacological activity as described in the previously cited work in J. Med. Chem., 12, 487–490, (1969) or in the previously cited patents of Chiesi Farmaceutici S.p.A. and SIMES Società Italiana Medicinali e Sintetici S.p.A.

The steps which regard the process of the present invention shall now be described in detail.

Step A

The condensation reaction between 2,3-dimethoxybenzaldehyde and pyruvic acid in the presence of a base to yield 4-(2,3-dimethoxyphenyl)-2-oxo-3-butenoic acid is well known.

In the literature this condensation reaction is performed in the presence of an inorganic base such as sodium hydroxide [Hudson et al., J. Chem. Soc., 715–722, (1941)] or potassium carbonate [Pavel et al., Acta Univ. Palacki Olomuc. Fac. Rerum. Natur., 401–404, (1971)-C.A.]. However, performing the reaction with inorganic bases produces the desired product (compound III) with a low yield. In particular, a yield of approximately 40% is obtained using sodium hydroxide and in the case of potassium carbonate a yield of only 6% is obtained. We have now found that performing the condensation reaction between 2,3-dimethoxybenzaldehyde and pyruvic acid in the presence of an organic base compound (III) is obtained with a high yield (approximately 80%), which is of obvious industrial interest.

Suitable organic bases are triethylamine, piperidine, piperazine and morpholine.

The organic base can be used in excess in a suitable solvent system or used itself as the solvent.

The use of piperidine is preferred.

Step B

This step consists of the transformation of the ketonic group of compound (III) to an amino group and the reduction of the double bond.

The transformation is performed by initially condensing the ketonic group with a suitable nitrogenous nucleophilic agent, such as ammonium hydroxide, hydroxylamine or hydrazine, and then reducing the product formed in accordance with conventional procedures, such as catalytic hydrogenation.

The reduction of the condensation reaction product results in the concomitant reduction of the double bond.

Purely for practical purposes, it is preferred to condense compound (III) with hydroxylamine, thereby obtaining the corresponding oxime which, by catalytic hydrogenation, is then reduced to the amino group together with the concomitant reduction of the double bond.

This results in the compound of formula (IV).

Alternatively, it is obvious that the reduction of the double bond could be initially performed on compound (III) to obtain the corresponding saturated alpha-ketonic acid of the formula:

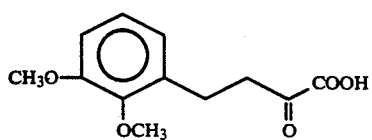

(III-A)

after which the ketonic group can be transformed to the amino group according to the aforementioned procedure. This alternative method is of particular interest when an enantio-selective transformation of the ketonic group is required.

For example, compound (III-A) can be condensed with a suitable arylcarboxyamide to obtain the corresponding enamide, which can be thereby reduced as described by J. Haplam in Asymmetric Synthesis, 5, 41–69, J. D. Morrison Ed., Academic Press Inc.

Using this method, compound (IV) is obtained in an optically active form.

Similarly, the preparation of compound (IV) in an optically active form can also be carried out by resolution of the racemic mixture of compound (IV) using conventional techniques such as separating the diastereomeric salts.

Step C

This step consists of the cyclization of compound (IV) with the concomitant protection of the amino group.

The reaction is carried out with trifluoroacetic anhydride in trifluoroacetic acid.

This step is of particular importance.

In fact, to the best of our knowledge, no methods have been described in the literature to perform, in a single step, the concomitant protection of the amino group of an amino acid together with intramolecular cyclization.

The method commonly described in the literature consists of initially protecting the amino group, usually by acylation with a trihaloacetic anhydride, and preferably with trifluoroacetic anhydride, followed by a Friedel-Crafts cyclization using, for example, phosphorus pentoxide and phosphoric acid, phosphorus pentachloride or aluminium chloride [see Varie, David L., Tetrahedron Lett., 31(52), 7583–6, (1990) or the European patent No. 0286515 (Adir et Compagnie)].

We have found that the reaction of compound (IV) with trifluoroacetic anhydride in trifluoroacetic acid involves the concomitant protection of the amino group and the intramolecular cyclization to obtain, in a single step, 5,6-dimethoxy-2-trifluoroacetylamino-1-tetralone (compound V).

Moreover, this reaction is of particular industrial interest since it can be performed with a high yield, above 80% in practice.

It is important to underline that the reaction conditions allow the cyclization and protection of compound (IV) in an optically active form to thus obtain the corresponding enantiomer of compound (V).

Step D

This step consists of the reduction of compound (V), which can also be in an optically active form, to the corresponding compound (VI) using conventional procedures such as catalytic hydrogenation.

As far as we know this reaction has never been described for compound (V). Moreover, the reaction produces compound (VI) with a substantially quantitative yield.

Step E

Similarly, this step, which consists of deprotecting the amino group of compound (VI) to obtain 2-amino-5,6-dimethoxytetralin (compound VII), is performed using conventional procedures, such as treatment with bases or with sodium borohydride.

The process of the present invention has notable advantages. 2-amino-5,6-dimethoxy-tetralin is obtained in a racemic and optically active form with an extremely high overall yield.

In fact, every step has an industrially satisfactory yield, for the most part greater than 80% or even quantitative.

The starting materials and reagents are cheap and easily attainable and the reaction conditions can be easily applied industrially.

The following examples illustrate the present invention without limiting it in any way.

EXAMPLE 1

4-(2,3-dimethoxyphenyl)-2-oxo-3-butenoic acid

Into a flask, equipped with a mechanical stirrer, thermometer and a $CaCl_2$ valve, 2,3-dimethoxybenzaldehyde (500 g; 3.0 moles) and anhydrous dimethylformamide (1750 ml) were loaded under a nitrogen stream.

The solution obtained was cooled to 0°–5° C. and pyruvic acid (251 g; 2.85 moles) was added.

Maintaining the temperature at from 0° to 5° C., piperidine (383.17 g; 4.5 moles) was added dropwise as quickly as possible.

Upon completing the addition, the reaction mixture was heated to 20° C. in 10 minutes and maintained under stirring at 25° C. for 24 hours.

The reaction mixture was poured into water (7 l), washed with ethyl ether (3×1100 ml) and the aqueous phase was cooled to 5° C. and acidified to pH 1 with concentrated hydrochloric acid.

The solution was stirred for 1 hour at 5° C., the solid was filtered, washed twice with cold water and then dried in an oven at 70° C. in the presence of NaOH to obtain 4-(2,3-dimethoxyphenyl)-2-oxo-3-butenoic acid (519.9 g; yield, 77.2%), which was chromatographically pure (thin-layer chromatography-eluent $CH_2Cl_2:CH_3OH:CH_3COOH=79:15:1$).

m.p. 133°–135° C.

$^1$H-NMR (300 MHz, $CDCl_3$): delta (ppm): 3.89 (3H, s), 3.92 (3H, s); 7.03 (1H, dd); 7.11 (1H, t); 7.31 (1H, dd); 7.61 (1H, d); 8.42 (1H, d).

Mass Spectrum (chemical ionization, isobutane): 237 (M+1) I.R. (KBr): 1680–1710 $cm^{-1}$.

EXAMPLE 2

4-(2,3-dimethoxyphenyl)-2-hydroxyimino-3-butenoic acid

Into a flask, equipped with a mechanical stirrer, thermometer and a $CaCl_2$ valve, 4-(2,3-dimethoxyphenyl)-2-oxo-3-butenoic acid (500 g; 2.12 moles), prepared as described in example 1, was loaded under a nitrogen stream. To this, absolute ethanol (1000 ml) and piperidine (1020 ml) were added.

The reaction mixture was cooled to 15° C. and hydroxylamine hydrochloride (175 g; 2.55 moles) added in small portions.

The temperature of the reaction mixture was adjusted to 20° C. and maintained under stirring for 9 hours.

The reaction mixture was maintained at 4° C. overnight, then poured into a mixture of ice and water (5 l) and acidified to pH 1 with concentrated hydrochloric acid (1 L), maintaining the temperature below 10° C.

The precipitate formed was extracted with ethyl acetate (4×1000 ml) to obtain a waxy product (461 g; yield, 86.7%), which was then used for the following reactions.

Thin-layer chromatography (eluent $CH_2Cl_2:CH_3OH:CH_3COOH=79:15:1$) showed that the product was chromatographically pure and consists of two isomers syn and anti 4-(2,3-dimethoxyphenyl)-2-hydroxyimino-3-butenoic acid.

$^1$H-NMR (300 MHz, DMSO): delta (ppm): 3.70 (3H, s), 3.82 (3H, s); 7.05 (1H, dd); 7.10 (1H, t); 7.21 (1H, d); 7.22 (1H, dd); 7.74 (1H, d).

Mass Spectrum (chemical ionization, isobutane): 252 (M+1), 190 I.R. (KBr): 1680 $cm^{-1}$.

EXAMPLE 3

2-amino-4-(2,3-dimethoxyphenyl)-butanoic acid hydrochloride

A suspension of 4-(2,3-dimethoxyphenyl)-2-hydroxyimino-3-butenoic acid (50 g; 0.199 moles), prepared as described in example 2, acetic acid (950 ml) and concentrated hydrochloric acid (50 ml; 0.597 moles), in the presence of 10% Pd-on-charcoal catalyst (5 g), was hydrogenated in a Parr shaker apparatus under 2.72 atmospheres of pressure and at a temperature of 25° C.

Upon completing hydrogenation (after 3.5 hours), the catalyst was filtered off and washed with water.

The organic phase was evaporated to dryness under reduced pressure and the residue was slurried in ethyl acetate to obtain 2-amino-4-(2,3-dimethoxyphenyl)-butanoic hydrochloride (43.2 g; yield, 79%), which was chromatographically pure (thin-layer chromatography-eluent toluene:acetone:n.butanol: $H_2O:CH_3COOH=1:1:1:1:1$).

m.p. 180°–183° C.

$^1$H-NMR (300 MHz, DMSO): delta (ppm): 2.15 (2H, m); 2.78 (2H, m); 3.82 (3H, s), 3.84 (3H, s); 3.96 (1H, t); 6.80 (1H, dd); 6.91 (1H, dd); 7.01 (1H, t).

I.R. (KBr): 1740 $cm^{-1}$.

EXAMPLE 4

5,6-dimethoxy-2-trifluoroacetylamino-1,2,3,4-tetrahydronaphthalen-1-one

Into a flask, equipped with a mechanical stirrer, thermometer and a $CaCl_2$ valve, 2-amino-4-(2,3-dimethoxyphenyl)butanoic acid hydrochloride (400 g; 1.452 moles), prepared as described in example 3, and trifluoroacetic acid (4 l) were loaded under a nitrogen stream.

The solution obtained was cooled to −10° C. and trifluoroacetic anhydride (670.4 g; 3.192 moles) was added dropwise.

Upon completing the addition, the temperature was allowed to rise to 20° C. and the reaction mixture was maintained under stirring for 1 hour.

The reaction mixture was cooled to −10° C. and further trifluoroacetic anhydride (335.2 g; 1.596 moles) added dropwise.

Upon completing the addition, the temperature was allowed to rise to 20° C. and the reaction mixture was maintained under stirring at this temperature overnight.

The solvent was evaporated and the residue was suspended again in methanol (800 mL).

The crude material obtained was slurried with ethyl ether.

The suspension was cooled to 5°–10° C. and filtered, washing twice with cold ethyl ether, to obtain 5,6-dimethoxy-2-trifluoroacetylamino-1,2,3,4-tetra-hydronaphthalen-1-one (387.9 g; yield, 84.2%), which was chromatographically pure (thin-layer chromatography - eluent toluene:acetone:n.butanol:$H_2O:CH_3COOH=1:1:1:1:1$).

m.p. 159°–161° C.

¹H-NMR (300 MHz, CDCl₃): delta (ppm); 1.86 (1H, m), 2.93 (2H, m); 3.30 (1H, m); 3.84 (3H, s); 3.95 (3H, s); 4.55 (1H, dt); 6.93 (1H, d); 7.56 (1H, bs); 7.84 (1H, d).

Mass Spectrum (chemical ionization, isobutane): 318 (M+1)

I.R. (KBr): 1680–1705 cm⁻¹.

EXAMPLE 5

5,6-dimethoxy-2-trifluoroacetylamino-1,2,3,4-tetrahydronaphthalene

A suspension of 5,6-dimethoxy-2-trifluoroacetylamino-1,2,3,4-tetrahydronaphthalen-1-one (200 g; 0.630 moles), prepared as described in example 4, in absolute ethanol (3.5 l) and 70% perchloric acid (20 g) was hydrogenated in an autoclave, in the presence of 10% Pd-on-charcoal catalyst (20 g), at 29.6 atmospheres of pressure and a temperature of 20° C. for 24 hours.

The catalyst was filtered off and the solution dried.

The residue was dissolved in ethyl acetate (1.5 l) and the solution washed once with a saturated solution of NaHCO₃ (150 mL; pH 8) and once with water.

After drying on Na₂SO₄, the solvent was evaporated to obtain 5,6-dimethoxy-2-trifluoroacetylamino-1,2,3,4-tetrahydronaphthalene (188 g; yield, 98.4), which was chromatographically pure (thin-layer chromatography - eluent n.hexane:ethyl acetate=4:1).

m.p. 112°–113° C.

¹H-NMR (300 MHz, CDCl₃): delta (ppm); 1.81 (1H, m), 2.10 (1H, m); 2.68 (1H, dd); 2.82 (1H, ddd); 2.95 (1H, dt); 3.10 (1H, dd); 3.81 (3H, s); 3.84 (3H, s); 4.28 (1H, m); 6.40 (1H, bs); 6.76 (1H, d); 6.80 (1H, d).

Mass Spectrum (chemical ionization, isobutane): 304 (M+1)

I.R. (KBr): 1690 cm⁻¹.

EXAMPLE 6

2-amino-5,6-dimethoxy-1,2,3,4-tetrahydronaphthalene hydrochloride

Into a flask, equipped with a methanical stirrer, thermometer and a CaCl₂ valve, 5,6-dimethoxy-2-trifluoroacetylamino-1,2,3,4-tetrahydronaphthalene (400 g; 1.319 moles), prepared as described in example 5, was loaded under a nitrogen stream.

Absolute ethanol (3 l) was added and, to the resultant solution, sodium borohydride (99.79 g; 2.638 moles) was added in small portions over a period of 3 hours, maintaining a temperature of 20° C.

The reaction mixture was maintained under stirring for 3 hours and again sodium borohydride (99.79 g; 2.638 moles) was added in small portions over a period of 2 hours, always maintaining the temperature at 20° C.

The mixture was kept under stirring overnight at the same temperature and then cooled to 0° C. Carefully, concentrated hydrochloric acid (617.4 mL; 7.254 moles) was then added dropwise, maintaining the temperature at from 10° to 15° C. and diluting the slurry with ethanol (700 mL) when necessary.

A solid was obtained which was filtered off and the mother liquor then dried to a residue.

The residue thus obtained and the filtered solid were combined, taken up with water (2.7 l) and made basic with a 40% solution of NaOH (195.4 mL) up to sharply basic pH.

After extraction with CH₂Cl₂ (1 × 1 l and 3 × 500 mL) and drying on Na₂SO₄, the solvent was evaporated to obtain a residue which was then redissolved in ethyl acetate (1 l). The mixture was acidified with an ethereal solution saturated with hydrochloric acid to thus obtain by precipitation 2-amino-5,6-dimethoxy-1,2,3,4-tetrahydronaphthalene hydrochloride (yield, 90%).

m.p. 278°–280° C.

¹H-NMR (300 MHz, DMSO): delta (ppm): 1.66 (1H, m); 2.10 (1H, m); 2.55–2.75 (2H, m), 2.90 (1H, ddd); 2.99 (1H, dd); 3.35 (1H, m); 3.67 (3H, s); 3.75 (3H, s); 6.83 (1H, d); 6.87 (1H, d).

Mass Spectrum (chemical ionization, isobutane): 208 (M+1)

I.R. (KBr): 1090 cm⁻¹.

EXAMPLE 7

4-(2,3-dimethoxyphenyl)-2-oxo-butanoic acid

To a mixture of 4-(2,3-dimethoxyphenyl)-2-oxo-3-butenoic acid (1 g; 4.23 mmoles), prepared as described in example 1, and ethanol (42 mL) 10% Pd-on-charcoal catalyst (100 mg) was added.

The mixture was hydrogenated at room temperature for 1 hour.

After having filtered off the catalyst and evaporated the solvent under reduced pressure, a crude mixture was obtained which was purified chromatographically using a column of silica gel (eluent, methylene chloride:methanol=9:1) to form pure 4-(2,3-dimethoxyphenyl)-2-oxo-butanoic acid (630 mg; yield, 62%).

¹H-NMR (300 MHz, CDCl₃): delta (ppm): 2.73 (2H, t), 2.80 (2H, t); 3.70 (3H, s); 3.78 (3H, s); 6.76 (1H, d); 6.86 (1H, d); 6.95 (1H, t).

We claim:

1. A process for the preparation of 2-amino-5,6-dimethoxytetralin comprising
A) condensing 2,3-dimethoxy-benzaldehyde with pyruvic acid, in the presence of a base, to form 4-(2,3-dimethoxyphenyl)-2-oxo-3-butenoic acid,
B) transforming the ketonic group of 4-(2,3-dimethoxyphenyl)-2-oxo-3-butenoic acid and reducing the double bond to obtain 2-amino-4-(2,3-dimethoxyphenyl)-butanoic acid,
C) cyclizing, with trifluoroacetic acid and trifluoroacetic anhydride, 2-amino-4-(2,3-dimethoxyphenyl)-butanoic acid to an amino group with concomitant protection of the amino group to form 5,6-dimethoxy-2-trifluoroacetylamino-1-tetralone,
D) reducing the ketonic group of 5,6-dimethoxy-2-trifluoroacetylamino-1-tetralone to yield 5,6-dimethoxy-2-trifluoroacetylamino-tetralin, and
E) deprotecting the amino group of 5,6-dimethoxy-2-trifluoroacetylamino-tetralin to obtain 2-amino-5,6-dimethoxy-tetralin.

2. A process according to claim 1, wherein the condensation of 2,3-dimethoxybenzaldehyde with pyruvic acid is performed in the presence of an organic base.

3. A process according to claim 1, wherein the transformation of the ketonic group is performed by condensing it with a suitable nitrogenous nucleophilic agent.

4. A process for the preparation of 2-amino-5,6-dimethoxytetralin comprising
C) cyclizing, with trifluoroacetic acid and trifluoroacetic anhydride, 2-amino-4-(2,3-dimethoxyphenyl)-butanoic acid with concomitant protection of the amino group to form 5,6-dimethoxy-2-trifluoroacetylamino-1-tetralone,
D) reducing the ketonic group of 5,6-dimethoxy-2-trifluoroacetylamino-1-tetralone to yield 5,6-dimethoxy-2-trifluoroacetylamino-tetralin, and
E) deprotecting the amino group of 5,6-dimethoxy-2-trifluoroacetylamino-tetralin to obtain 2-amino-5,6-dimethoxy-tetralin.

* * * * *

UNITED STATES PATENT AND TRADEMARK OFFICE
CERTIFICATE OF CORRECTION

PATENT NO. : 5,221,770
DATED : June 22, 1993
INVENTOR(S) : Giorgio Bertolini et al.

It is certified that error appears in the above-indentified patent and that said Letters Patent is hereby corrected as shown below:

On the title page, Item [73],

The assignee's city is spelled incorrectly, should read:

--Vicenza--

Signed and Sealed this

Fourth Day of January, 1994

*Attest:*

BRUCE LEHMAN

*Attesting Officer*      *Commissioner of Patents and Trademarks*